United States Patent [19]
Scholl

[11] Patent Number: 5,913,860
[45] Date of Patent: Jun. 22, 1999

[54] SURGICAL NAIL INSERTER

[75] Inventor: Christopher Hargest Scholl, West Chester, Pa.

[73] Assignee: Synthes (USA), Paoli, Pa.

[21] Appl. No.: 09/031,751

[22] Filed: Feb. 27, 1998

[51] Int. Cl.[6] .................................................. A61B 17/56
[52] U.S. Cl. .......................................... 606/100; 606/86
[58] Field of Search ............................ 606/99, 100, 104, 606/86

[56]  References Cited

U.S. PATENT DOCUMENTS

| | | | |
|---|---|---|---|
| 3,094,021 | 6/1963 | Young | 813/52.3 |
| 3,208,450 | 9/1965 | Abelson | 128/83 |
| 3,334,624 | 8/1967 | Schnider et al. | 128/92 |
| 3,585,994 | 6/1971 | Huggler | 128/83 |
| 3,750,500 | 8/1973 | Peterson | 810/52.35 |
| 4,222,382 | 9/1890 | Antonsson et al. | 606/100 |
| 4,462,395 | 7/1984 | Johnson | 606/100 |
| 4,476,861 | 10/1984 | Dimakos et al. | 606/100 |
| 4,924,056 | 5/1990 | Bevilacqua | 219/98 |
| 5,156,606 | 10/1992 | Chin | 606/100 |
| 5,417,696 | 5/1995 | Kashuba et al. | 606/99 |
| 5,476,467 | 12/1995 | Benoist | 606/100 |
| 5,505,732 | 4/1996 | Michelson | 606/61 |

*Primary Examiner*—Michael Buiz
*Assistant Examiner*—Daphna Shai
*Attorney, Agent, or Firm*—Pennie & Edmonds LLP

[57]  ABSTRACT

A device and method for the insertion and removal of an internal fracture fixation implant are disclosed. The device includes a slide rod having a tubular body with first and second ends and a bore for receiving the implant, a securing element located on the first end of the slide rod for maintaining the implant in the bore, a handle on the second end of the slide rod for manipulation of the device, and a slap hammer having a body member configured and dimensioned to be releasably and slideably connected to the slide rod so that displacement against the securing element results in impaction while displacement against the handle results in extraction of the implant. Removing the slap hammer from the slide rod when it is not needed facilitates use of the device. In a preferred embodiment, the slap hammer has a grip and the slap hammer body member has a channel for receiving the slide rod and at least one retaining element for maintaining the slide rod in the channel. Preferably, the grip is pivotally connected to the body member of the slap hammer to increase the handling of the device. The securing element can be a keyless chuck that has a variable opening that accommodates implants having diameters ranging from 0.6 to 6 mm. Although the chuck can be tightened or loosened by hand, slots on the chuck allow tool-assisted tightening or loosening.

16 Claims, 2 Drawing Sheets

SURGICAL NAIL INSERTER

FIELD OF THE INVENTION

The present invention is directed to a surgical tool for impacting and extracting an implant used for the internal fixation of a bone fracture.

BACKGROUND OF THE INVENTION

The internal fixation of a fractured long bone using an elongated nail, pin, or wire is frequently desirable. However, it is difficult to drive the nail into both halves of the fracture so that the fractured portions are properly aligned in close apposition.

A wide variety of surgical instrumentation has been developed to facilitate the internal fixation of fractures. For example, U.S. Pat. No. 5,476,467 discloses a surgical hammer for driving K-wires. The tool disclosed in this patent can only accommodate a limited number of sizes of wires and the collet must be changed for each wire size. Another disadvantage of the tool is that the slap hammer cannot be removed from the tool. Manipulating the tool with the extra weight of the slap hammer is cumbersome. Further, unwanted movement of the slap hammer could interfere with proper implantation of the wire.

Thus, there exists a need for an improved device for the impaction and extraction of an internal fracture fixation implant.

SUMMARY OF THE INVENTION

The present invention relates to a device for impaction and extraction of an implant into bone. The device comprises a slide rod having a tubular body with first and second ends and a bore for receiving the implant, a securing element located on the first end of the slide rod for maintaining the implant in the bore, a handle on the second end of the slide rod for manipulation of the device, and a slap hammer having a body member configured and dimensioned to be releasably and slideably connected to the slide rod so that displacement against the securing element results in impaction while displacement against the handle results in extraction of the implant. It is preferred that the securing element is a keyless chuck that has a variable opening that accommodates implants having diameters ranging from 0.6 to 6 mm. Although the chuck can be tightened or loosened by hand, slots on the chuck allow tool-assisted tightening or loosening. In a preferred embodiment, the slap hammer has a grip and the slap hammer body member has a channel for receiving the slide rod and at least one retaining element for maintaining the slide rod in the channel. Preferably, the grip is pivotally connected to the body member of the slap hammer. In a preferred embodiment, the retaining element comprises a ball plunger biased to partially protrude into the channel by a spring and held in place by a threaded body. Contact by the slide rod forces the ball plunger out of the channel to allow the slide rod to slideably engage the channel.

The present invention also relates to a method for impacting or extracting an implant into bone of a patient. The method includes the steps of: configuring a slide rod to have a tubular body with first and second ends and a bore for receiving the implant; providing a securing element on one end of the slide rod and a handle on the other end; associating an implant with the slide rod by engaging a portion of the implant with the securing member; releasably connecting a slap hammer to the slide rod; and displacing the body member of the slide rod either against the securing element to impact the implant into the bone or against the handle to extract the implant from the bone. In one embodiment, the implant is initially associated with the slide rod and the method includes positioning and placing the implant in the patient's body before releasably connecting the slap hammer to the slide rod. In another embodiment, an entry point is drilled for insertion of the implant and the implant is initially positioned and placed in the patient's body and then engaged with the securing member. The method also includes the step of visualizing the implant during the impaction or extraction using a radiographic imaging system. As the implant is impacted or extracted the portion of the implant engaged with the securing member is adjusted.

DESCRIPTION OF THE PREFERRED EMBODIMENTS

Figure 1:
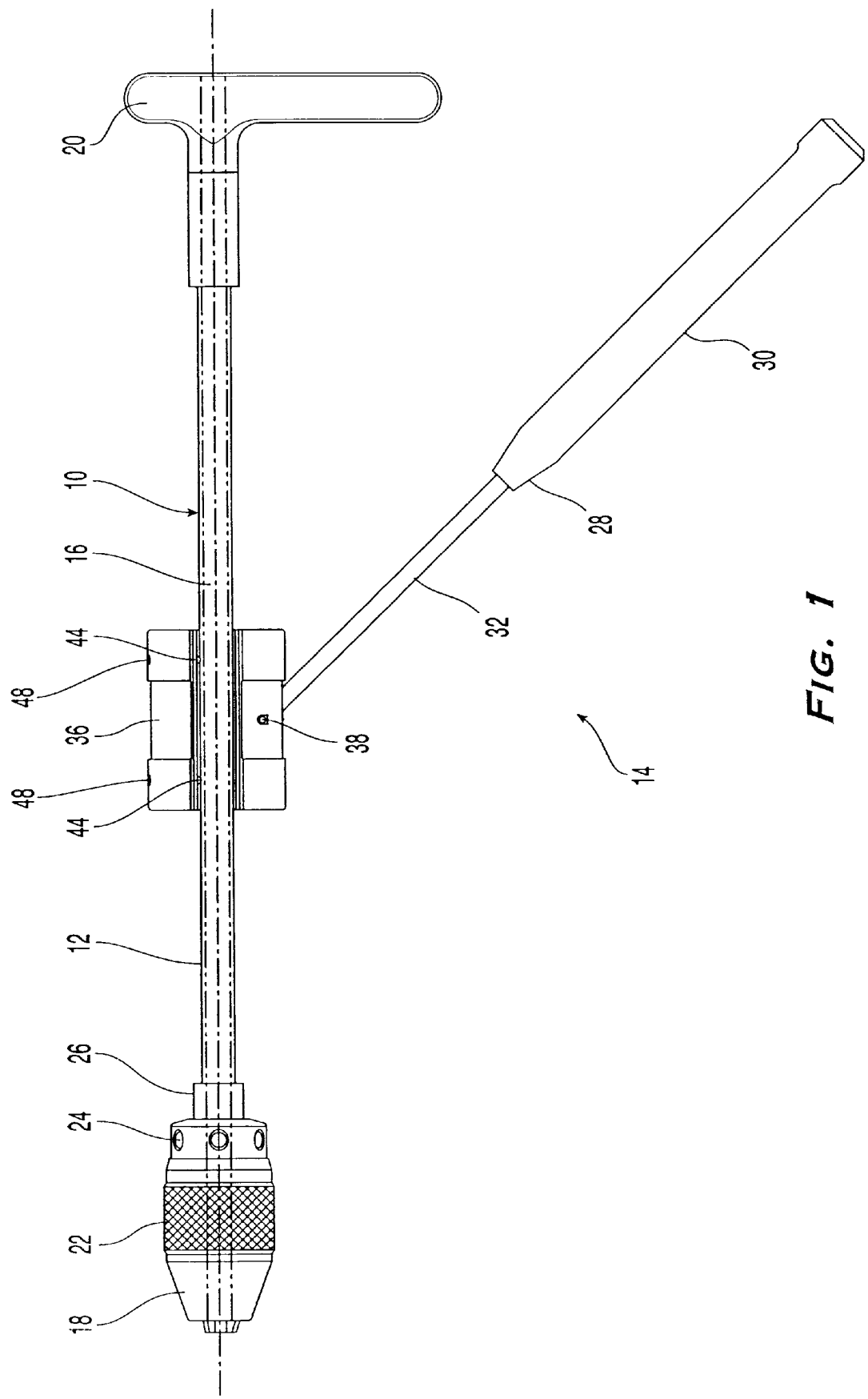
FIG. 1 is a plan view of the device according to the present invention.
Figures 2, 3:
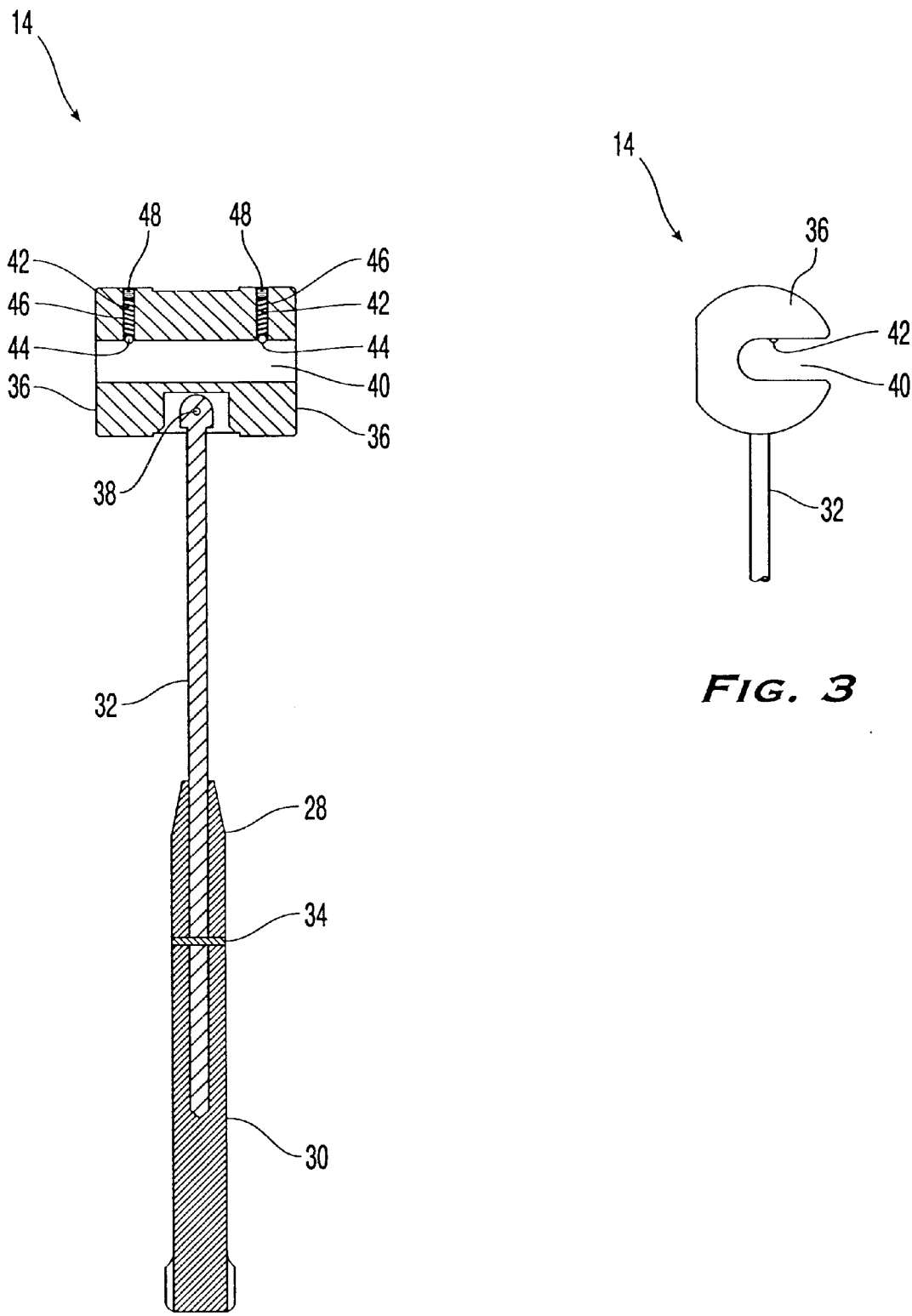
FIG. 2 is a cross-sectional view of a slap hammer according to the present invention.
FIG. 3 is an end view of a body member of the slap hammer.

FIG. 1 shows the surgical nail inserter 10 according to the present invention. Inserter 10 has a slide rod 12 and a slap hammer 14. Slide rod 12 is a tube that has a bore 16 for receiving an implant, such as a nail. The inserter 10 can also be used with a wire, pin, or other implants. Inserter 10 can even be used with a reaming rod, i.e., instrumentation used to guide a reamer for preparing the medullary canal prior to insertion of an intermedullary nail. One end of slide rod 12 has a chuck 18 for securing the implant in bore 16 and the other end has a handle 20. Handle 20 is shown as a L-shaped handle, but any configuration which would allow a surgeon to control and rotate inserter 10 can be used. The rotation of inserter 10 is desirable so that the implant can be twisted during impaction or extraction. The twisting motion controls the direction of the implant. Thus, if the implant has a feature such as curved tip, the surgeon can ensure that the feature is properly oriented. Preferably, handle 20 is open-ended so that bore 16 extends the full length of inserter 10, and, if needed, the implant can protrude through handle 20.

Chuck 18 is a keyless chuck that can accommodate implants of various sizes. Typically, the implant would have a diameter of 0.6 to 6 mm. As chuck 18 is keyless, it can be tightened and loosened by hand. Thus, intraoperative changing of the portion of the implant that is held by chuck 18 is facilitated. This allows a surgeon to easily move the implant through bore 16 as the implant is impacted or extracted. As some implants are specifically designed to be flexible, it is important that the portion of the implant anterior to chuck 18 not be too long to avoid bending of the implant. Raised surface 22 provides the surgeon a surer grip while twisting chuck 18. Slots 24 are sized to receive a tool such as a wrench for situations in which the surgeon wishes to supplement hand tightening or loosening.

After an implant has been inserted in bore 16 and chuck 18 has been tighten, the movement of slap hammer 14 against collar 26 provides the driving force for impaction. Collar 26 is optional and slap hammer 14 could directly contact chuck 18 if desired. The use of collar 26 is preferred to reduce the force of the impaction to avoid damage to chuck 18. In an analogous fashion, the movement of slap hammer 14 against handle 20 provides the driving force for extraction.

Slap hammer 14 can be removed from slide rod 12 to increase the manageability of inserter 10. Slap hammer 14 has a grip member 28 that includes a gripping portion 30 and a connecting portion 32. Gripping and connecting portions 30, 32 are joined by a rivet 34. Connecting portion 32 is attached to a body member 36 by pin 38 in such a manner that body member 36 can pivot about grip member 28. The ability of body member 36 to pivot about grip member 28 increases the maneuverability of inserter 10. Body member 36 is substantially cylindrical in shape with a flattened side and has a channel 40 sized to receive slide rod 12. Channel 40 has two retaining elements 42 that maintain slide rod 12 in channel 40 while still permitting slap hammer 14 to slide along slide rod 12. Retaining elements 42 are positioned in channel 40 so that when slap hammer 14 is attached to slide rod 12, slide rod 12 rests against the surfaces of channel 40 and retaining elements 42. Retaining element 42 consists of a ball plunger 44 that partially protrudes into channel 40, a spring 46 for spring loading ball plunger 44, and a threaded body 48 for holding ball plunger 44 and spring 46 in place.

In order to connect slap hammer 14 to slide rod 12, the surgeon inserts slide rod 12 into channel 40. In so doing, slide rod 12 contacts the portion of ball plungers 44 that protrudes into channel 40. The contact force is sufficient to compress springs 46 and cause all of ball plunger 44 to be clear of channel 40 so that slide rod 12 can be seated in channel 40. When slide rod 12 is seated in channel 40, spring 46 forces the protruding portion of ball plunger 44 back into channel 40, and thus maintains slide rod 12 in channel 40. In order to remove slap hammer 14 from slide rod 12, the surgeon simply moves slide rod 12 laterally in channel 40. The contact pressure of slide rod 12 against ball plunger 44 is sufficient to overcome the biasing of spring 46 and clear channel 40 of ball plunger 44.

As previously noted, the movement of slap hammer 14 against collar 26 provides the driving force for impaction and the movement of slap hammer 14 against handle 20 provides the driving force for extraction. Providing inserter 10 with grip member 28 and handle 20 separates the surfaces the surgeon uses to hold inserter 10 from the surfaces that slap hammer 14 strikes. Simultaneous rotation or turning and impaction or extraction of the implant is made possible by handle 20, grip member 28, and the manner in which slap hammer 14 attaches to slide rod 12.

A method of fixing a fracture using the surgical nail inserter according to the present invention will now be described using the fixation of a diaphyseal femoral fracture in a child as an example.

The surgeon first selects the proper nail diameter. The appropriate diameter depends upon a number of factors including the bone being fixed, the number of nails used to fix the fracture, and the size of the medullary isthmus. The medullary isthmus can be determined using standard imaging techniques. Once the nail is selected, the fracture is reduced. The reduction of the fracture should be confirmed with fluoroscopy in both the anterior-posterior and medial-lateral views. Fluoroscopy can also be used to ascertain the placement of the surgical incision for the entry point of the nail. After the incision has been made and the soft tissue has been dissected and retracted to expose the bone, the surgeon drills the entry point. Inserter 10 can also be used without creating an entry point with a drill. The desirability of drilling an entry point will depend on a number of factors including the patient's bony stock, the implant, and the surgical technique.

Once the desired angle of the entry point has been created, the surgeon inserts an end of the nail into the entry point by hand. Alternatively, the nail can already be secured in bore 16 of slide rod 12 by chuck 18 and the surgeon uses inserter 10 to introduce the nail into the entry point. After the nail has been secured to inserter 10 and introduced into the entry point, the surgeon fluoroscopically determines if the nail needs to be rotated to align the curved tip so that the convex side will properly glance off the far cortex. If the nail does need to be rotated, the surgeon does so by turning handle 20.

The surgeon attaches slap hammer 14 to slide rod 12 in the manner described above. The movement of slap hammer 14 against collar 26 provides the driving force for impaction and advancement of the nail through the medullary canal. The surgeon monitors the advance of the nail with fluoroscopy. The nail is advanced until the fracture site is reached. If another nail is to be used, the second nail should be inserted on the opposite side of the first nail up to the level of the fracture.

With the fracture reduced, the nail is driven across the fracture using fluoroscopy for visualization. The nail can be rotated using handle 20 so that its curved tip can spear the opposite fragment of the fracture. If the nail needs to be rotated, it is easier to do so while the nail is being advanced or retracted rather than when the nail is stationary. If the nail does not successfully cross the fracture gap, the movement of slap hammer 14 against handle 20 provides the driving force for extraction of the nail so that another attempt to cross the fracture gap can be made. Providing inserter 10 with grip member 28 and handle 20 separates the surfaces the surgeon uses to hold inserter 10 from the surfaces that slap hammer 14 strikes. Simultaneous rotation or directing and impaction or extraction of the nail is made possible by handle 20, grip member 28, and the manner in which slap hammer 14 attaches to slide rod 12. Once the nail captures the opposite fragment, the nail position can be confirmed using both anterior-posterior and medial-lateral views. If a second nail is used, it can now be advanced across the gap.

When the nail is in its final position, chuck 18 can be loosened to remove the nail from inserter 10. After the fracture has healed or the surgeon otherwise determines that the nail should be removed, inserter 10 can be used to facilitate the explantation process.

While it is apparent that the illustrative embodiments of the invention herein disclosed fulfil the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. A device for impaction and extraction of an implant into bone comprising:
   a slide rod having a tubular body with first and second ends and a bore for receiving an implant;
   a securing element located on the first end of the slide rod for maintaining the implant in the bore;
   a handle on the second end of the slide rod for manipulation of the device; and
   a slap hammer having a body member configured and dimensioned to be releasably and slideably connected to the slide rod so that displacement of the body member against the securing element results in impaction of the implant while displacement of the body member against the handle results in extraction of the implant,
   wherein the slap hammer can be releasably connected to or removed from the slide rod to facilitate placement and positioning of the implant; and wherein the slap hammer body member includes a channel therein having a sidewall along a longitudinal axis of the channel, a portion of which is open for accommodating the slide rod.

2. The device of claim 1, wherein the securing element is a chuck having an opening which is variable in size for conforming to the implant.

3. The device of claim 2, wherein the opening is 0.6–6 mm and the chuck has at least one slot for receiving a tool for adjusting the opening.

4. The device of claim 1, wherein the slap hammer body member includes at least one retaining element for maintaining the slide rod in the channel.

5. The device of claim 4, wherein the at least one retaining element comprises a ball plunger biased to partially protrude into the channel by a spring, said spring and ball plunger held by a threaded body, wherein contact by the slide rod forces the ball plunger out of the channel to allow the slide rod to slideably engage or disengage the channel.

6. The device of claim 1, wherein the slap hammer further comprises a grip member that is pivotally connected to the body member of the slap hammer.

7. The device of claim 1, wherein the handle is L-shaped to facilitate rotation of the slide member.

8. The device of claim 1, wherein the second end of the slide rod is open so that the implant can extend therethrough.

9. A method for impacting or extracting an implant into bone of a patient which comprises:

configuring a slide rod to have a tubular body with first and second ends and a bore for receiving an implant;

providing a securing element on one end of the slide rod and a handle on the other end;

associating an implant with the slide rod by engaging a portion of the implant with the securing member;

releasably connecting a slap hammer to the slide rod, where the slap hammer includes a body member configured and dimensioned to be releasably and slideably connected to the slide rod, and a channel therein having a sidewall along a longitudinal axis of the channel, a portion of which is open for accommodating the slide rod; and displacing the body member of the slide rod either against the securing element to impact the implant into the bone or against the handle to extract the implant from the bone.

10. The method of claim 9 wherein the implant is initially associated with the slide rod and which further comprises positioning and placing the implant in the patient's body before releasably connecting the slap hammer thereto.

11. The method of claim 9 which further comprises initially positioning and placing the implant in the patient's body and then engaging the implant with the securing member.

12. The method of claim 9 which further comprises removing the slap hammer from the slide rod after impacting or extracting the implant.

13. The method of claim 9 which further comprises configuring the slap hammer to include a grip member to facilitate displacement of the body member.

14. The method of claim 9 which further comprises adjusting the portion of the implant engaged with the securing member as the implant is impacted or extracted from the bone.

15. The method of claim 9 which further comprises visualizing the implant during impacting or extracting using a radiographic imaging system.

16. The method of claim 9 which further comprises drilling an entry point for insertion of the implant.

* * * * *